United States Patent [19]

van Andel

[11] Patent Number: Plant 5,525

[45] Date of Patent: Jul. 30, 1985

[54] CARNATION NAMED STANGELLA

[75] Inventor: Jacob van Andel, Aalsmeer, Netherlands

[73] Assignees: B. V. Handelskwekerij; M. C. van Staaveren, both of Aalsmeer, Netherlands

[21] Appl. No.: 556,614

[22] Filed: Nov. 30, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Chas. W. Rummler

[57] ABSTRACT

A new miniature carnation variety having light yellow flowers of medium size which are produced continuously on strong, upright flower stems, this plant being distinguished by producing a larger number of smaller flowers per flower stem than is normally found in common miniature carnation varieties, the plant itself having a vigorous, strong and upright growth habit with normal branching character and abundant foliage.

1 Drawing Figure

BACKGROUND OF THE NEW PLANT

This new miniature carnation variety originated as a seedling of unknown parentage growing among a collection of miniature carnations maintained in greenhouse at Aalsmeer, Holland, for breeding purposes and was discovered by me in the course of my periodic inspection of greenhouse facilities maintained at Aalsmeer, Holland, for commercial and breeding purposes. This new variety attracted my attention because of the very large number of blooms carried by each flowering stem which, of course, is a very advantageous characteristic, and for that reason, I propagated this discovery plant by means of cuttings and upon finding the results to be quite favorable, I continued propagation in that manner through several successive generations to observe its overall growth and flowering habits and I found that its novel and advantageous characteristics held true from generation to generation and appeared to be firmly fixed.

DESCRIPTION OF THE DRAWING

This new variety of miniature carnation plant is illustrated by the accompanying photographic drawing, which has been partially hand painted to show the specified color, and which shows, the upper portions of several flowering stems, the view showing buds and flowers in vasious stages of growth from new bud to fully opened flower.

DESCRIPTION OF THE NEW PLANT

The following is a detailed description of my new miniature carnation variety based upon observation of greenhouse grown plants made at Aalsmeer, The Netherlands, in the summer of 1983, the color designations being according to The R.H.S. Colour Chart published by The Royal Horticultural Society of London, England.

THE PLANT

Origin: Seedling.
Parentage: Unknown.
Classification:
- *Botanic.*—Hybrid *Dianthus caryophyllus.*
- *Commercial.*—Miniature carnation.

Form: Bush.
Height: Various depending upon season.
Growth rate: Rapid, vigorous and strong with normal branching characteristic.
Foliage:
- *Quantity.*—Abundant.
- *Number of leaves.*—Depends upon season.
- *Size of leaf.*—Medium.
- *Texture.*—Smooth.
- *Color.*—Upper side and under side — Grey/Green.

THE BUD

Size: Normal.
- *Diameter.*—About 10 mm.
- *Length.*—About 20 1 mm.

Shape: Initially pointed ovoid becoming generally cylindrical before sepals divide.
Rate of opening: Moderate.
Color of petals:
- *When sepals first divide.*—Light Yellow.

Sepals:
- *Shape.*—Generally rectangular with upper ends of oval character and acuminate tips normally hooded over the bud.
- *Character.*—Sepals stand up when the flowers open.
- *Color.*—Inside and outside — Grey/Green.

Calyx: Funnel-shaped and long.
- *Aspect.*—Smooth.
- *Splitting.*—The calyx does not split.

Flower stem:
- *Length.*—Long.
- *Color.*—Grey/Green.

THE FLOWER

Blooming habit: Continuous.
Size of bloom: Medium for miniatures.
- *Diameter.*—About 40 mm.
- *Depth.*—About 20 mm.

Shape: High centered when bloom first opens and as the bloom matures.
Petalage:
- *Number of petals.*—Approximately 30.
- *Arrangement.*—Loosely overlapping.
- *Texture.*—Soft.
- *Appearance.*—Shiny.

*Color.*—Both outer and inner petals: Upper side — Body — R.H.S. 2C/3C. Base — Pale Green. Reverse side — R.H.S. 2C/3C. Colors are the same for all seasons.

Flower stem:

*Length.*—Depends upon season.

*Character.*—Strong and upright.

*Color.*—Grey/Green.

Persistence: Petals hang on and dry.

Fragrance: Very weak.

Disease resistance: Less susceptible to *Fusarium oxysporum* as observed in the area of Aalsmeer, Holland.

Lasting quality:

*On plant.*—Approximately 20 days.

*As cut flower.*—Approximately 12 days.

REPRODUCTIVE ORGANS

Stamens:

*Number.*—Medium.

*Anthers.*—Size: Medium. Color: Yellow.

*Filaments.*—Color: White.

*Pollen.*—There is no pollen.

Pistils:

*Number.*—One.

*Style.*—Length: Approximately 35 mm. Color: White.

*Stigma.*—Color: White/Cream.

This new miniature carnation variety is particularly characterized by the larger number of smaller flowers borne on each flowering stem and by its very rapid and excellent flower production.

I claim:

1. The new and distinct variety of miniature carnation, substantially as herein shown and described, characterized by its continuous production of blooms and its rapid growth rate, the larger number of blooms per flowering stem than is normal for miniature carnations, and its apparent resistance to *Fusarium oxysporum.*

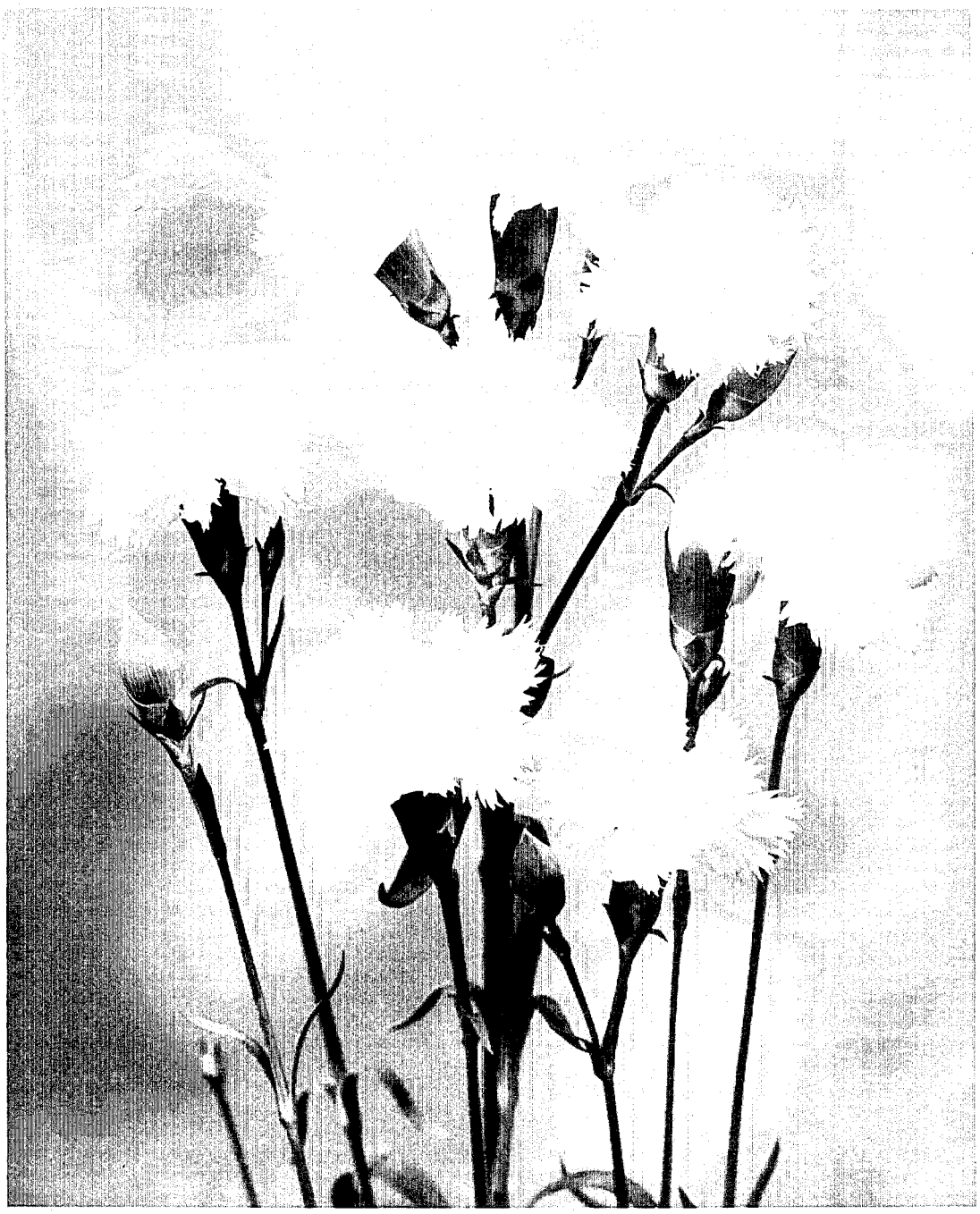

* * * * *